(12) United States Patent
Lee et al.

(10) Patent No.: US 12,273,985 B2
(45) Date of Patent: Apr. 8, 2025

(54) VOLTAGE GENERATING APPARATUS AND X-RAY GENERATING APPARATUS HAVING THE SAME

(71) Applicant: REMEDI CO., LTD, Chuncheon-si (KR)

(72) Inventors: Re Na Lee, Seoul (KR); Young Hwan Kim, Seoul (KR); Sung Ho Cho, Seoul (KR); Hyun Jun Kim, Seoul (KR)

(73) Assignee: REMEDI CO., LTD (KR)

( * ) Notice: Subject to any disclaimer, the term of this patent is extended or adjusted under 35 U.S.C. 154(b) by 0 days.

(21) Appl. No.: 17/925,603

(22) PCT Filed: Nov. 3, 2022

(86) PCT No.: PCT/KR2022/017143
§ 371 (c)(1),
(2) Date: Nov. 15, 2022

(87) PCT Pub. No.: WO2023/204367
PCT Pub. Date: Oct. 26, 2023

(65) Prior Publication Data
US 2024/0237182 A1    Jul. 11, 2024

(30) Foreign Application Priority Data
Apr. 21, 2022 (KR) .......... 10-2022-0049726

(51) Int. Cl.
*H05G 1/32* (2006.01)
*H05G 1/10* (2006.01)
(Continued)

(52) U.S. Cl.
CPC .............. *H05G 1/32* (2013.01); *H05G 1/10* (2013.01); *H05G 1/20* (2013.01); *H05G 1/265* (2013.01); *H05G 1/56* (2013.01)

(58) Field of Classification Search
CPC .. H05G 1/32; H05G 1/10; H05G 1/20; H05G 1/56
See application file for complete search history.

(56) References Cited

U.S. PATENT DOCUMENTS

| | | | |
|---|---|---|---|
| 2009/0046911 A1* | 2/2009 | Inoue ............ | A61B 6/481 382/130 |
| 2016/0143120 A1* | 5/2016 | Shindo .......... | A61B 6/032 378/93 |
| 2024/0224407 A1* | 7/2024 | Lee .............. | H05G 1/265 |

FOREIGN PATENT DOCUMENTS

| | | | |
|---|---|---|---|
| JP | 2019102348 A | 6/2019 | |
| JP | 2019103204 A | 6/2019 | |

(Continued)

OTHER PUBLICATIONS

English translation of JP 2019-102348 A (Year: 2019).*
(Continued)

*Primary Examiner* — Chih-Cheng Kao
(74) *Attorney, Agent, or Firm* — Renaissance IP Law Group LLP

(57) ABSTRACT

The present inventive concept provides a voltage generating apparatus for X-rays including a console that receives an X-ray irradiation signal to generate a control signal and detects the X-ray irradiation signal to generate a first detection signal, a pulse control unit that receives the control signal and the first detection signal from the console to generate a second detection signal and generates a pulse signal according to the control signal and the second detection signal, and a high voltage generating unit that generates a high voltage according to the pulse signal from the pulse control unit, and an X-ray generating apparatus having the same.

12 Claims, 4 Drawing Sheets

(51) Int. Cl.
  H05G 1/20  (2006.01)
  H05G 1/26  (2006.01)
  H05G 1/56  (2006.01)

(56)  References Cited

FOREIGN PATENT DOCUMENTS

| KR | 19990039675 A | 6/1999 |
| KR | 100731506 B1 | 6/2007 |
| KR | 20090030531 A | 3/2009 |
| KR | 20140045471 A | 4/2014 |
| KR | 101529041 B1 | 6/2015 |
| KR | 101742571 B1 | 6/2017 |

OTHER PUBLICATIONS

Kim, Young-Pyo et al., "Characteristic Evaluation of Medical X-Ray Using High-Voltage Generator with Inverter System", J. Kieeme, vol. 24, No. 1, pp. 36-41, Jan. 2011.

Kim, Young-Pyo et al., "Development of High Voltage Generator for Diagnostic X-ray Equipment", Proceedings of the Korean Institute of Information and Communication Sciences Conference, 2010. 10a, pp. 764-765, Oct. 27, 2010.

Notification of Transmittal of Translation of the International Preliminary Report on Patentability including Written Opinion mailed Oct. 31, 2024.

* cited by examiner

ＶＯＬＴＡＧＥ ＧＥＮＥＲＡＴＩＮＧ ＡＰＰＡＲＡＴＵＳ ＡＮＤ X-RAY GENERATING APPARATUS HAVING THE SAME

TECHNICAL FIELD

The present disclosure relates to an X-ray generating apparatus, and more particularly, to a voltage generating apparatus for X-rays capable of preventing a malfunction due to component damage, and an X-ray generating apparatus including the same.

BACKGROUND ART

An X-ray system can image the inside of a human body in a non-invasive way, and thus is generally used for diagnosis and treatment in medical institutions, and has been developed to enable more convenient and precise use thanks to the development of advanced technology. In addition, the X-ray system is being used to observe an internal shape of a subject in the field of non-destructive testing as well as in the medical field.

The X-ray system uses the principle that when the subject is irradiated with X-rays, the degree of absorption of X-rays differs depending on the difference in density of substances inside the subject. Here, since a tissue with a high density absorbs more X-rays than a tissue with a low density, when the tissue with a high density is observed on an X-ray photosensitive film or a detector after the X-ray is transmitted through a living tissue, the tissue with a high density appears black compared to the tissue with a low density. Accordingly, it is possible to clearly distinguish a structure of an internal tissue of the subject depending on to the difference in density.

Such an X-ray system may be generally configured to include an X-ray tube that generates X-rays, a voltage generating apparatus that generates and supplies a high voltage required for the X-ray tube, an X-ray detecting apparatus that detects X-rays that have passed through the subject, and a control device that controls an operation of the X-ray tube and the voltage generating apparatus. Here, the voltage generating apparatus and the X-ray tube form the X-ray generating apparatus, and a predetermined signal according to a tube voltage, tube current, irradiation time, etc., which are appropriately calculated, is supplied to the X-ray tube from the voltage generating apparatus. The X-ray tube causes hot electrons emitted from a cathode to collide with an anode target at high speed according to a predetermined signal supplied from the voltage generating apparatus to generate X-rays by braking radiation.

In order to generate a high voltage applied to the X-ray tube, a voltage generating apparatus that generates a high voltage by increasing a power supply frequency from several tens to hundreds of times using an inverter is being used. For example, a voltage generating apparatus using a pulse width modulation (PWM) scheme is used. This pulse width modulation scheme has the advantages of higher performance of photographing, miniaturization of a power supply, and stable output generation, compared to the existing transformer method.

In the pulse width modulation voltage generating apparatus, when an X-ray irradiation signal is applied from an X-ray irradiation switch, a control signal for device operation such as on/off, tube voltage, tube current, and irradiation time of the X-ray system is generated, and a DC high voltage is generated according to a pulse signal and applied to the X-ray tube after the pulse signal of a predetermined width is generated according to the control signal.

By the way, in the case of a conventional voltage generating apparatus, a malfunction may occur when an internal circuit component is damaged. That is, a circuit component inside the voltage generating apparatus may be damaged and short-circuited with a ground terminal. In this case, an unintentional X-ray irradiation signal is transmitted. Accordingly, X-rays may be generated in an unintended situation and the subject may be irradiated with X-rays. For example, when the subject is not located in the X-ray system, even when the subject is not located in a correct position of the X-ray system, X-rays are generated and thus, a problem such as an inspection error may occur.

PRIOR ART LITERATURE

Patent literature: Korean Patent Registration No. 10-1529041

Non-patent literature: Kim Young-pyo et al. (2010), Development of high-voltage generator for diagnostic X-ray equipment, Fall Conference of the Korean Society of Maritime Information and Communication Sciences 2010, pp. 764-765.

DISCLOSURE OF THE INVENTIVE CONCEPT

Technical Problem

The present inventive concept provides a voltage generating apparatus capable of preventing a malfunction and an X-ray generating apparatus having the same.

The present inventive concept provides a voltage generating apparatus capable of preventing a malfunction due to damage to an internal circuit component and an X-ray generating apparatus having the same.

The present inventive concept provides a voltage generating apparatus that operates by detecting an X-ray irradiation switch, thereby capable of preventing a malfunction, and an X-ray generating apparatus having the same

Technical Solution

A voltage generating apparatus according to an aspect of the present inventive concept includes a console that receives an X-ray irradiation signal to generate a control signal and detects the X-ray irradiation signal to generate a first detection signal, a pulse control unit that receives the control signal and the first detection signal from the console to generate a second detection signal and generates a pulse signal according to the control signal and the second detection signal, and a high voltage generating unit that generates a high voltage according to the pulse signal from the pulse control unit.

The console includes a first control unit that receives the X-ray irradiation signal to generate a control signal, and a first signal detecting unit that detects the X-ray irradiation signal to generate a first detection signal.

The first control unit generates first and second control signals, respectively, and the first signal detecting unit generates the first detection signal according to a level of the X-ray irradiation signal.

The pulse control unit includes a second signal detecting unit that receives the first control signal and the first detection signal from the console and combines the first control signal and the first detection signal to generate a second detection signal, a second control unit that receives the second control signal from the console and receives the second detection signal from the second signal detecting unit to generate third and fourth control signals, a converter that converts the third control signal from the second control unit, and a pulse generating unit that receives an output signal from the converter and the fourth control signal from the second control unit to generate a pulse signal.

The pulse control unit further includes a first input unit that receives the second control signal, a second input unit that receives the first control signal, and a switch that applies the pulse signal to the high voltage generating unit.

The second signal detecting unit generates the second detection signal of a predetermined level according to the first control signal and the first detection signal each having a predetermined level or higher.

The second signal detecting unit generates the second detection signal of a predetermined level when the X-ray irradiation signal is equal to or greater than a predetermined level and the first detection signal is greater than or equal to a predetermined level.

The second signal detecting unit includes a high-pass filter that receives the first detection signal, and at least one AND gate that combines an output of the high-pass filter and an output of the second input unit, and the second detection signal is generated as an output of the AND gate.

The second control unit receives the second control signal from the console and the second detection signal from the second signal detecting unit to generate third and fourth control signals and outputs the third and fourth control signals to the pulse generating unit, respectively.

The pulse generating unit receives the third control signal from the second control unit, the output signal from the converter, and a feedback signal from the high voltage generating unit to generate the pulse signal.

The high voltage generating unit includes a transformer that generates a high voltage to be applied to an X-ray tube according to the pulse signal from the pulse control unit, a high voltage switch that controls an application of the high voltage generated from the transformer to the X-ray tube, a voltage detecting unit that detects the high voltage applied to the X-ray tube and feeds the high voltage back to the pulse generating unit, and a current detecting unit that detects a current of the X-ray tube.

An X-ray generating apparatus according to another aspect of the present inventive concept includes a voltage generating apparatus that generates a predetermined voltage according to an X-ray irradiation signal, and an X-ray tube that generates X-rays according to a voltage from the voltage generating apparatus, and the voltage generating apparatus includes a signal detecting unit that detects the X-ray irradiation signal to generate a detection signal, and generates a predetermined voltage according to the X-ray irradiation signal and the detection signal.

The voltage generating apparatus includes a console that receives the X-ray irradiation signal to generate a control signal and detects the X-ray irradiation signal to generate a first detection signal, a pulse control unit that receives the control signal and the first detection signal from the console to generate a second detection signal and generates a pulse signal according to the control signal and the second detection signal, and a high voltage generating unit that generates a high voltage according to the pulse signal from the pulse control unit.

The console includes a first control unit that receives the X-ray irradiation signal to generate the first and second control signals, respectively, and a first signal detecting unit that detects the X-ray irradiation signal to generate a first detection signal.

The pulse control unit includes a second signal detecting unit that receives the first control signal and the first detection signal from the console and combines the first control signal and the first detection signal to generate a second detection signal, a second control unit that receives the second control signal from the console and receives the second detection signal from the second signal detecting unit to generate third and fourth control signals, a converter that converts the third control signal from the second control unit, and a pulse generating unit that receives an output signal from the converter and the fourth control signal from the second control unit to generate a pulse signal.

The second signal detecting unit outputs the first detection signal, which is input through a high-pass filter, and the first control signal through at least one AND gate to generate the second detection signal.

The voltage generating apparatus includes a console that receives the X-ray irradiation signal to generate a control signal, a pulse control unit that receives the control signal from the console to generate a detection signal and generates a pulse signal according to the control signal and the detection signal, and a high voltage generating unit that generates a high voltage according to the pulse signal from the pulse control unit.

The console includes a first control unit that receives the X-ray irradiation signal to generate first and second control signals, respectively.

The pulse control unit includes a second control unit that receives first and second control signals from the console to generate third and fourth control signals, respectively, and detects at least one of the first and second control signals to generate a first detection signal, a signal detecting unit that receives the fourth control signal and the first detection signal and combines the fourth control signal and the first detection signal to generate a second detection signal, a converter that converts a third control signal from the second control unit, and a pulse generating unit that receives an output signal from the converter and the second detection signal from the second signal detecting unit to generate a pulse signal.

Advantageous Effects

In the voltage generating apparatus for X-rays of the present inventive concept, the console can detect an X-ray irradiation signal to generate a predetermined detection signal, and a pulse control unit can detect the detection signal from the console to control generation of a pulse signal. That is, in the present inventive concept, when both the first control signal and the detection signal from the console are applied at high levels, the pulse control unit can generate the second detection signal and apply the second detection signal to the high voltage generating unit. In the present inventive concept, since the second detection signal is generated according to the first detection signal and the first control signal and the pulse signal for generating a high voltage is generated accordingly, a malfunction due to damage to components constituting the console and/or the pulse control unit can be prevented. That is, conventionally, since the pulse control unit operates only with a control signal, a malfunction has occurred due to damage to the components constituting the console and/or the pulse control unit. However, in the present inventive concept, since the pulse signal is generated according to the control signal and the detection signal generated according to the X-ray irradiation signal, erroneous generation of the pulse signal can be prevented, and accordingly, the malfunction of the X-ray generating apparatus can be prevented.

MODE FOR CARRYING OUT THE INVENTIVE CONCEPT

Figure 1:
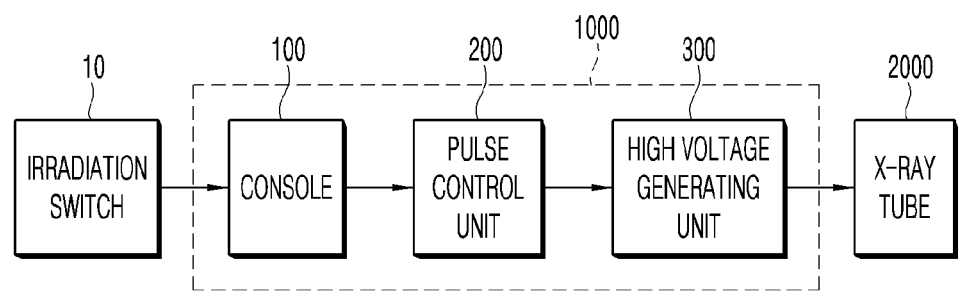
FIG. 1 is a block diagram for describing a configuration of an X-ray generating apparatus including a voltage generating apparatus and an X-ray tube according to an embodiment of the present inventive concept.

Hereinafter, specific embodiments will be described in detail with reference to the accompanying drawings. The present inventive concept may, however, be embodied in different forms and should not be construed as limited to the embodiments set forth herein. Rather, these embodiments are provided so that this disclosure will be thorough and complete, and will fully convey the scope of the present inventive concept to those skilled in the art.

In the figures, the dimensions of layers and regions are exaggerated for clarity of illustration. Like reference numerals refer to like elements throughout. It will also be understood that when a layer, a film, a region or a plate is referred to as being 'on' another one, it can be directly on the other one, or one or more intervening layers, films, regions or plates may also be present. Further, it will be understood that when a layer, a film, a region or a plate is referred to as being 'under' another one, it can be directly under the other one, and one or more intervening layers, films, regions or plates may also be present. In addition, it will also be understood that when a layer, a film, a region or a plate is referred to as being 'between' two layers, films, regions or plates, it can be the only layer, film, region or plate between the two layers, films, regions or plates, or one or more intervening layers, films, regions or plates may also be present.

Hereinafter, an embodiment of the present inventive concept will be described in detail with reference to the accompanying drawings. However, the present inventive concept is not limited to the embodiments disclosed below, but will be implemented in various different forms, and only these embodiments are provided to complete the disclosure of the present inventive concept, and to fully inform those of ordinary skill in the art of the scope of the invention. In order to clearly express multiple layers and each region in the drawing, the thickness thereof is enlarged and expressed, and the same reference numerals refer to the same elements in the drawing.

Figure 2:
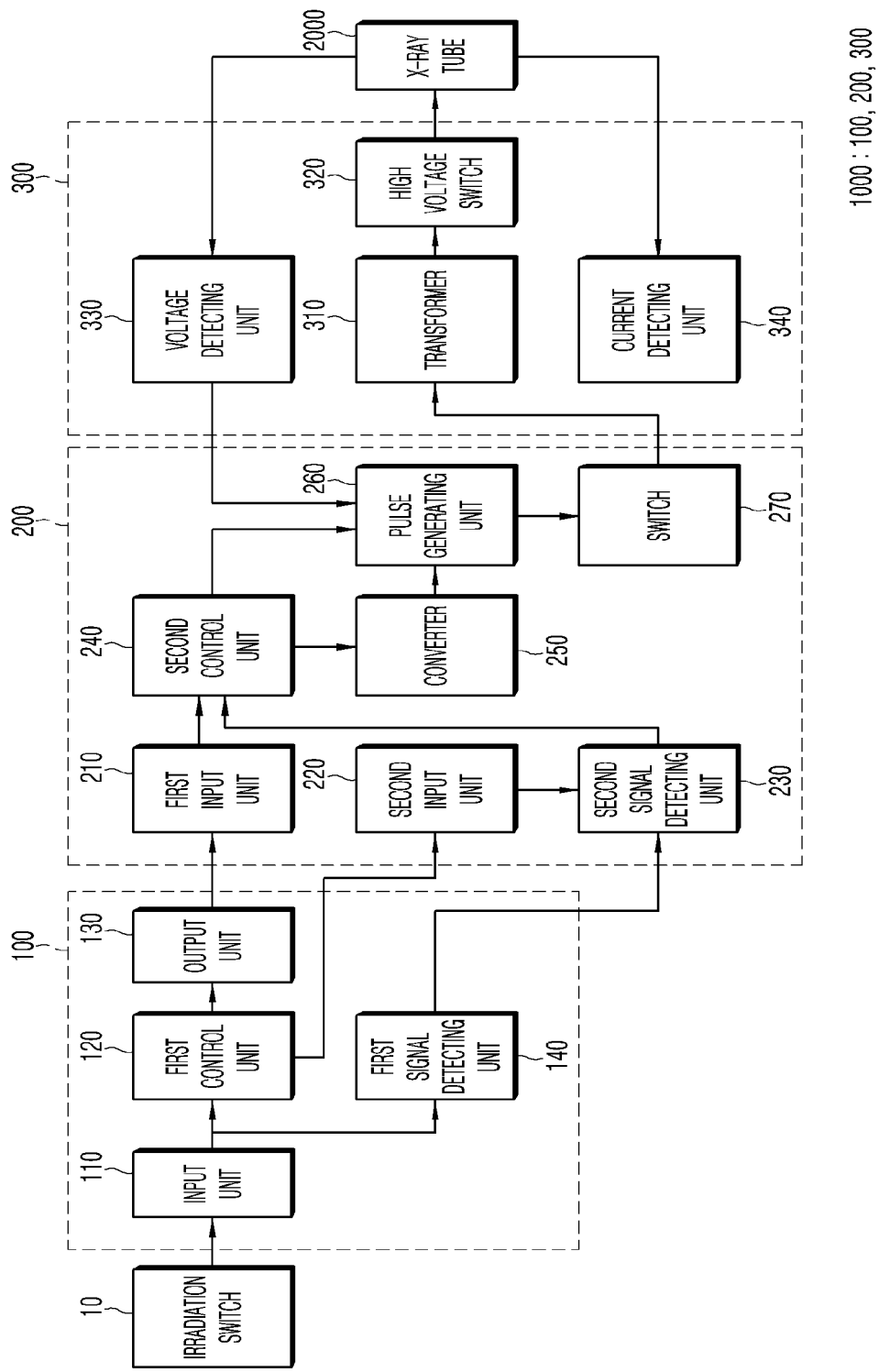
FIG. 2 is a block diagram for describing a detailed configuration of each part of the voltage generating apparatus according to an embodiment of the present inventive concept.
Figure 3:
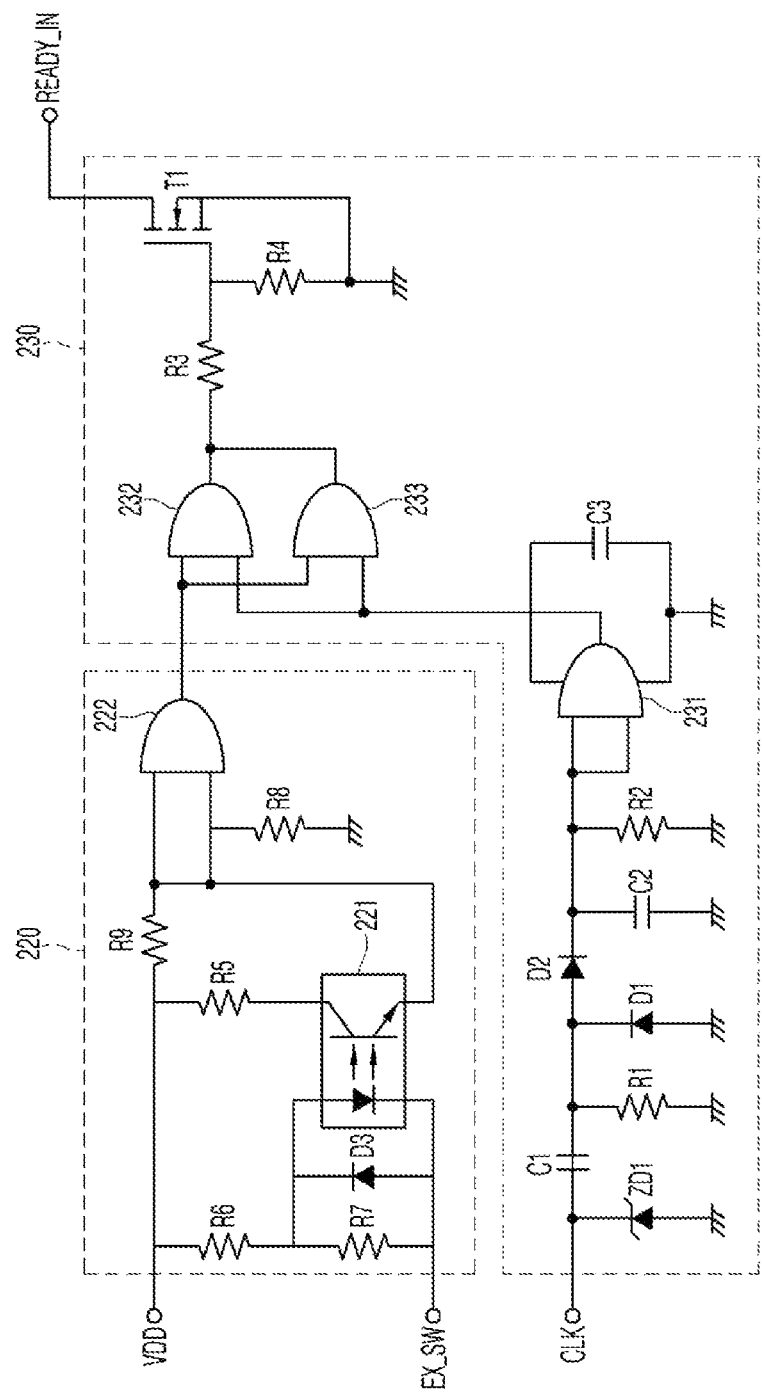
FIG. 3 is a circuit diagram of a signal detecting unit according to an embodiment of the present inventive concept constituting the voltage generating apparatus.
Figure 4:
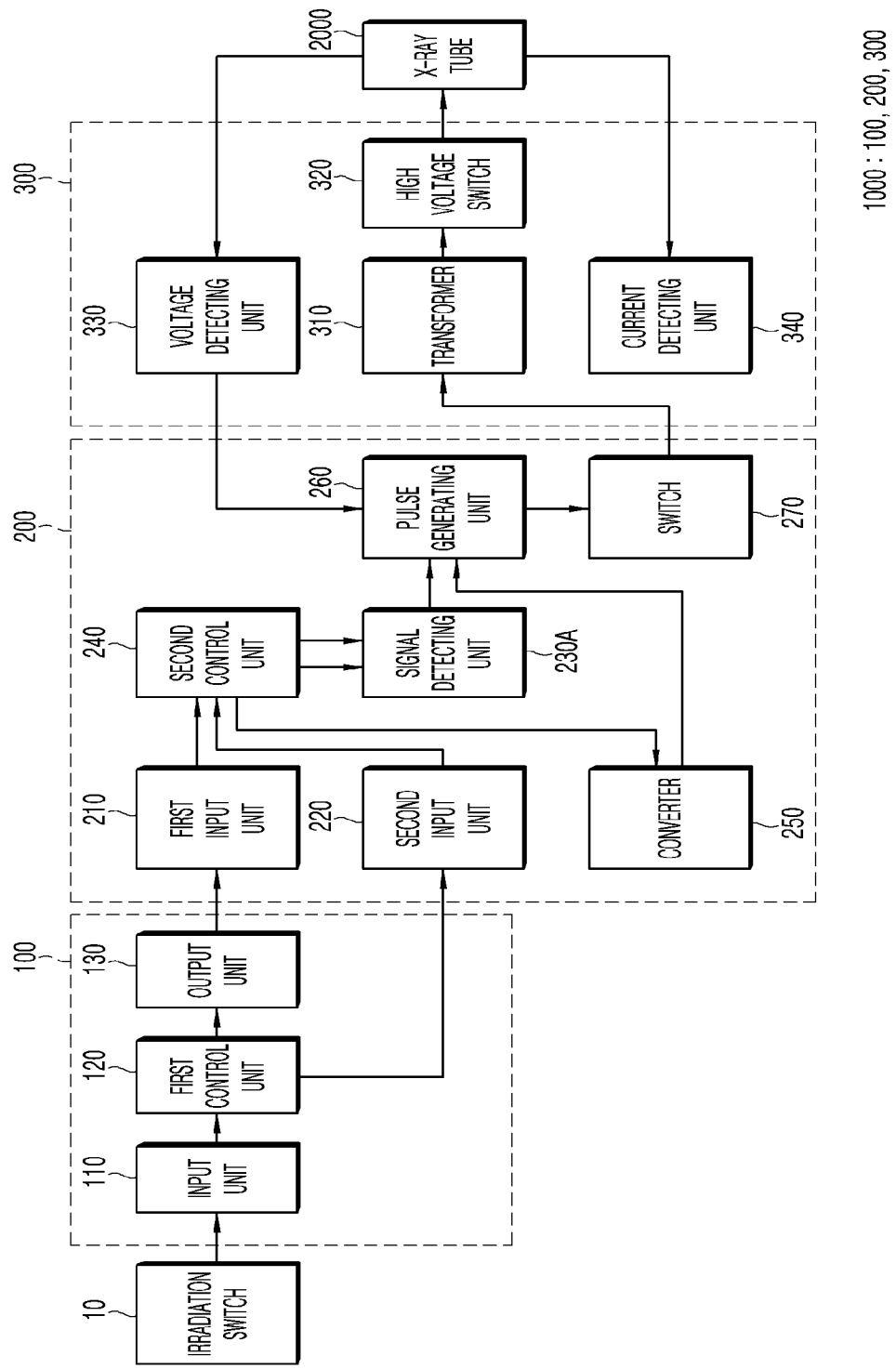
FIG. 4 is a block diagram for describing a detailed configuration of each part of a voltage generating apparatus according to another embodiment of the present inventive concept.

FIG. 1 is a block diagram for describing a configuration of an X-ray generating apparatus including a voltage generating apparatus and an X-ray tube according to an embodiment of the present inventive concept. Further, FIG. 2 is a block diagram for describing a detailed configuration of each part of the voltage generating apparatus according to an embodiment of the present inventive concept, and FIG. 3 is a circuit diagram of a signal detecting unit according to an embodiment of the present inventive concept constituting the voltage generating apparatus. FIG. 4 is a block diagram for describing a detailed configuration of each part of a voltage generating apparatus according to another embodiment of the present inventive concept.

Referring to FIG. 1, an X-ray generating apparatus according to an embodiment of the present inventive concept may include a voltage generating apparatus 1000 and an X-ray tube 2000, and the voltage generating apparatus 1000 for X-rays may include a console 100, a pulse control unit 200, and a high voltage generating unit 300 as illustrated in FIGS. 2 and 4. The X-ray generating apparatus according to the embodiments of the present inventive concept will be described in more detail for each configuration as follows.

1. Voltage Generating Apparatus

The voltage generating apparatus 1000 generates a predetermined voltage and supplies the predetermined voltage to the X-ray tube 2000. That is, the voltage generating apparatus 1000 generates a predetermined voltage for generating X-rays in the X-ray tube 2000. The voltage generating apparatus according to the embodiments of the present inventive concept may generate a voltage using a pulse width modulation (PWM) scheme. The voltage generating apparatus 1000 according to the embodiments of the present inventive concept of such a pulse width modulation scheme may include a console 100 that receives an X-ray irradiation signal from an X-ray irradiation switch 10 to generate a control signal for on/off, tube voltage, tube current, irradiation time of the X-ray generating apparatus, etc., and detects the X-ray irradiation signal to generate a first detection signal, a pulse control unit 200 that receives the control signal and the first detection signal from the console 100 to generate a pulse signal of a predetermined width modulated depending on the tube voltage, tube current, and irradiation time according to the first detection signal, and a high voltage generating unit 300 that generates a DC high voltage according to the pulse signal from the pulse control unit 200 and applies the DC high voltage to the X-ray tube 2000. Here, in the voltage generating apparatus 1000 according to the present inventive concept, the console 100 may detect an X-ray irradiation signal to generate a predetermined detection signal, and the pulse control unit 200 may detect the detection signal from the console 100 to control generation of the pulse signal. To this end, in the present inventive concept, the console 100 further includes a first signal detecting unit that detects the X-ray irradiation signal to generate the detection signal, and the pulse control unit 200 may further include a second signal detecting unit that detects the control signal and the detection signal from the console 100.

1.1. Console

The console 100 generates a control signal for device operation, such as on/off, tube voltage, tube current, and irradiation time of the X-ray generating apparatus according to an operation of the X-ray irradiation switch 10. In addition, the console 100 detects the operation of the X-ray irradiation switch to generate a predetermined detection signal. This console 100 may include an input unit 110 that receives an irradiation signal from the X-ray irradiation switch 10, a first control unit 120 that generates a control signal for device operation such as on/off, tube voltage, tube current, and irradiation time of the X-ray system according to the X-ray irradiation signal transmitted from the input unit 110, an output unit 130 that outputs the control signal from the first control unit 120 to the pulse control unit 200, and a first signal detecting unit 140 that detects the X-ray irradiation signal transmitted from the input unit 110 to generate a predetermined first detection signal.

In this case, the first control unit 120 and the first signal detecting unit 140 may be provided in a microprocessor. That is, the microprocessor may detect the X-ray irradiation signal to generate the first detection signal, and generate the control signal for device operation such as on/off, tube voltage, tube current, and irradiation time of the X-ray generating apparatus according to the X-ray irradiation signal.

1.1.1. Input Unit

When the X-ray irradiation signal is generated according to the operation of the X-ray irradiation switch 10, the input unit 110 receives the X-ray irradiation signal and transmits the X-ray irradiation signal to the first control unit 120. Here, the input unit 110 may include a photocoupler that transmits an electrical signal as light. That is, the input unit 110 may be formed of a photocoupler, and accordingly, an electric signal according to the X-ray irradiation signal may be transmitted as light to the first control unit 120.

1.1.2. First Control Unit

The first control unit 120 generates a control signal for device operation such as on/off, tube voltage, tube current, and irradiation time of the X-ray generating apparatus.

In this case, the first control unit 120 may generate a first control signal for on/off of the X-ray generating apparatus and may generate a second control signal for device operation such as the tube voltage, the tube current, and the irradiation time. That is, the first control unit 120 may generate the first and second control signals separately. The first control unit 120 generates the first control signal for turning on or off the X-ray generating apparatus according to the X-ray irradiation signal input through the input unit 110. That is, when a user presses the X-ray irradiation switch 10, the X-ray irradiation signal is applied at a high level, for example, and the first control unit 120 that has received the high-level X-ray irradiation signal through the input unit 110 generates a first control signal of high level for turning on the X-ray generating apparatus. In contrast, if the user does not press the X-ray irradiation switch 10, the first control unit 120 receives a signal of low level through the input unit 110, and the first control unit 120 generates a first control signal of low level for turning off the X-ray generating apparatus. That is, the first control unit 120 may generate the first control signal at a level according to the X-ray irradiation signal. When the X-ray irradiation signal is input at the high level, the first control unit 120 generates the first control signal of the high level, and generates the first control signal of the low level when the X-ray irradiation signal is input at the low level. In addition, the first control unit 120 may generate a second control signal. When the X-ray irradiation signal is input at a high level, the first control unit 120 may generate the second control signal such as the tube voltage, the tube current, and the irradiation time depending on a preset condition. In this case, the first control unit 120 may be provided in the microprocessor and may generate the second control signal for driving the X-ray generating apparatus depending on a preset condition according to the X-ray irradiation signal.

1.1.3. Output Unit

The output unit 130 outputs the control signal from the first control unit 120 to the pulse control unit 200. That is, the output unit 130 outputs the second control signal depending on operating conditions such as the tube voltage, the tube current, and the irradiation time of the X-ray generating apparatus to the pulse control unit 200. The output unit 130 may transmit the second control signal to the pulse control unit 200 through a predetermined communication method, for example, may output the second control signal through a serial communication scheme (RS232: recommended standard 232). Meanwhile, the first control signal for turning on/off of the X-ray generating apparatus generated from the first control unit 120 may be output to the pulse control unit 200 without passing through the output unit 130.

1.1.4. First Signal Detecting Unit

The first signal detecting unit 140 detects the X-ray irradiation signal input through the input unit 110 to generate a predetermined first detection signal. In this case, the first signal detecting unit 140 may generate a first detection signal of a pulse waveform in which a high level and a low level are repeated at a predetermined period, and may generate a first detection signal of high level or low level according to the level of the X-ray irradiation signal. That is, the first signal detecting unit 140 may generate a signal of high level or low level according to the level of the X-ray irradiation signal. The first signal detecting unit 140 may generate the signal of high level when the X-ray irradiation signal is applied at a high level, and generate the signal of low high level when the X-ray irradiation signal is applied at a low level.

1.2. Pulse Control Unit

The pulse control unit 200 receives the first and second control signals and the first detection signal from the console 100 to generate a pulse signal of a predetermined width modulated depending on the tube voltage, the tube current, and the irradiation time. In this case, when both the first control signal and the detection signal are applied at high levels from the console 100, the pulse control unit 200 may generate a predetermined pulse signal and apply the pulse signal to the high voltage generating unit 300. Since the pulse control unit 200 generates the pulse signal according to the detection signal and the first control signal, a malfunction due to damage to components constituting the console 100 and/or the pulse control unit 200 can be prevented. For example, a malfunction may occur due to damage to at least one of the input unit 110, which is composed of a photocoupler, of the console 10 and the second input unit 220, which is composed of the photocoupler, of the pulse control unit 200, and the first control unit 120, which is composed of a microprocessor, of the console 100 and a second control unit 240, which is composed of the microprocessor, of the pulse control unit 200, but, in the present inventive concept, since the pulse control unit 200 generates the pulse signal according to the detection signal and the first control signal, the malfunction can be prevented. That is, conventionally, since the pulse control unit 200 operates only with a control signal, a malfunction occurs due to damage to the components constituting the console 100 and/or the pulse control unit 200. However, in the present inventive concept, since the pulse signal is generated according to the control signal and the detection signal generated according to the X-ray irradiation signal, erroneous generation of the pulse signal can be prevented, and accordingly, the malfunction of the X-ray generating apparatus can be prevented. This pulse control unit 200 may include a first input unit 210 that receives a second control signal through the output unit 130 of the console 100, a second input unit 220 that receives the first control signal from the console 100, a second signal detecting unit 230 that receives the first control signal through the second input unit 220 and receives the first detection signal from the console 100 and combines the first control signal and the first detection signal to generate a second detection signal, a second control unit 240 that receives the second control signal from the first input unit 210 and receives the second detection signal from the second signal detecting unit 230 to generate third and fourth control signals, a converter 250 that performs D/A conversion on the third control signal from the second control unit 240, a pulse generating unit 260 that receives a converting signal from the converter 250 and the fourth control signal from the second control unit 240 and receives a tube voltage fed back from the X-ray tube 2000 to generate a pulse of a predetermined width, and a switch 270 that transmits the pulse signal of the pulse generating unit 260 to the high voltage generating unit 300.

1.2.1. First Input Unit

The first input unit 210 receives the second control signal from the console 100 and transmits the second control signal to the second control unit 240. That is, the first input unit 210 receives the second control signal according to operating conditions such as the tube voltage, the tube current, and the irradiation time of the X-ray generating apparatus from the output unit 130 of the console 100 and transmits the second control signal to the second control unit 240. The first input unit 210 may receive the second control signal from the output unit 130 in a predetermined communication scheme, and may receive the second control signal in the same communication scheme as the output unit 130 of the console 100. For example, the first input unit 210 may receive the second control signal through the serial communication scheme (RS232: recommended standard 232).

1.2.2. Second Input Unit

The second input unit 220 receives the first control signal from the console 100 and transmits the first control signal to the second signal detecting unit 230. That is, the second input unit 220 receives the first control signal for turning on/off the X-ray generating apparatus from the first control unit 130 of the console 100. Here, the second input unit 220 may include the photocoupler that transmits an electrical signal as light. That is, the second input unit 220 may be formed of the photocoupler, and thus may transmit an electrical signal according to the first control signal as light to the second signal detecting unit 230. Meanwhile, the second input unit 220 may include, as illustrated in FIG. 3, a voltage divider composed of first and second resistors R6 and R7, a photocoupler 221 that transmits the output of the second voltage divider as light, and an AND gate 222 that branches and receives the output signal of the photocoupler 221. Accordingly, the second input unit 220 may output a signal of high level when a control signal of high level is input.

1.2.3. Second Signal Detecting Unit

The second signal detecting unit 230 receives the first control signal from the second input unit 220 and the first detection signal from the console 100 to generate the second detection signal. That is, the second signal detecting unit 230 combines the output signal from the second input unit 220 and the first detection signal from the first signal detecting unit 140 of the console 100 to generate a second detection signal of a predetermined level. In this case, the second signal detecting unit 230 may output the second detection signal at a high level when the output signal from the second input unit 220 is at a high level and the first detection signal from the console 100 is at a high level. That is, the second signal detecting unit 230 may generate the second detection signal of high level when the X-ray irradiation signal is at a high level and the first detection signal according to the high level of the X-ray irradiation signal is at a high level. The second signal detecting unit 230 may be implemented using a passive element, and a circuit configuration of the second signal detecting unit 230 is illustrated in FIG. 3. As illustrated in FIG. 3, the second signal detecting unit 230 may be configured with resistors, capacitors, diodes, an AND gates, etc.

FIG. 3 is a circuit diagram of the second input unit 220 and the second signal detecting unit 230, and as illustrated in FIG. 3, the second signal detecting unit 230 may include an RC circuit and a plurality of logic elements. That is, the second signal detecting unit 230 may include a Zener diode ZD1, capacitors C1 and C2, diodes D1 and D2, resistors R1 and R2, and first to third AND gates 231, 232, and 233. Specifically, the second signal detecting unit 230 may include, for example, a Zener diode ZD1 connected between an input terminal of a first detection signal CLK input as a clock signal and a ground terminal, a first capacitor C1 connected to the input terminal of the first detection signal, the first resistor R1 and the first diode D1 connected in parallel between the first capacitor C1 and the ground terminal, the second diode D2 connected in parallel with the first diode D1 to the input terminal of the first detection signal, the second capacitor C2 and the second resistor R2 connected in parallel between the second diode D2 and the ground terminal, the first AND gate 231 to which the input terminal of the detection signal is branched and input, the second and third AND gates 232 and 233 that receive the output signal of the first AND gate 231 and the output signal of the second input unit 220, respectively, and a switch 234 that is turned on/off according to output signals of the second and third AND gates 232 and 233. Accordingly, the first detection signal CLK is input through a high-pass filter implemented as an RC circuit, and the output signal of the second input unit 220 is input, and these signals are output through the plurality of AND gates 231, 232, and 233 so that a second detection signal READY_IN may be output. That is, when both the first detection signal and the control signal are applied at the high level, the second detection signal may be output at the high level.

1.2.4. Second Control Unit

The second control unit 240 receives the second control signal from the first input unit 210 and receives the second detection signal from the second signal detecting unit 230 to generate a control signal. In this case, the second control unit 240 generates a third control signal for turning on/off the X-ray generating apparatus and outputs the third control signal to the pulse generating unit 260. That is, the second control unit 240 receives the first control signal from the console 100 to generate the third control signal, and outputs the third control signal to the pulse generating unit 260. In addition, the second control unit 240 generates a fourth control signal generated by setting the tube voltage, the tube current, the irradiation time, etc. In this case, the second control unit 240 generates the fourth control signal for generating a plurality of divided pulse signals according to the set tube voltage, tube current, irradiation time, etc. The fourth control signal is input to the converter 250 as a digital signal.

1.2.5. Converter

The converter 250 receives the second control signal generated from the second control unit 240 and converts the second control signal. That is, the converter 250 receives the fourth control signal for generating the pulse signal from the second control unit 240 to convert the fourth control signal into an analog signal. The analog signal generated in this way becomes a reference used for generating the tube voltage and tube current.

1.2.6. Pulse Generating Unit

The pulse generating unit 260 generates a predetermined pulse signal modulated depending on the control signal from the second control unit 240. In this case, the pulse generating unit 260 receives the third control signal for turning on/off the X-ray generating apparatus from the second control unit 240, and receives the analog signal through the converter 250 to generate a predetermined pulse signal. That is, the pulse generating unit 260 is driven according to the third control signal from the second control unit 240 to generate the predetermined pulse signal according to the analog signal from the converter 250. In addition, the pulse generating unit 260 receives a tube voltage feedback signal from the high voltage generating unit 300 and controls the pulse signal to always generate a uniform value after comparing the tube voltage feedback signal with an actual tube voltage. That is, the pulse generating unit 260 is driven according to the on/off signal of the X-ray generating apparatus and receives the analog control signal according to the tube voltage, the tube current, and the irradiation time from the converter 250 to generate the pulse signal, and compares the pulse signal generated by receiving the tube voltage feedback signal from the high voltage generating unit 300 with the actual tube voltage to always generate a uniform pulse signal.

1.2.7. Switch

The pulse signal generated by the pulse generating unit 260 is input to the high voltage generating unit 300 through the switch 270. In this case, the switch 270 may be configured as, for example, a full bridge SiC FET.

1.3. High Voltage Generating Unit

The high voltage generating unit 300 generates a DC high voltage according to the pulse signal from the pulse control unit 200, and applies the generated high voltage to the X-ray tube 2000. This high voltage generating unit 300 may include a transformer 310 that generates the DC high voltage to be applied to the X-ray tube 2000, a high voltage switch 320 that controls the application of the DC high voltage generated from the transformer 310 to the X-ray tube 2000, a voltage detecting unit 330 that detects a high voltage applied to the X-ray tube 2000, and a current detecting unit 340 that detects the current.

1.3.1. Transformer

The transformer 310 generates the DC high voltage to be applied to the X-ray tube 2000. The transformer 310 is an apparatus for generating a high voltage for generating high-speed kinetic energy in glass electrons, and for example, a 20 kHz LC resonance inverter type transformer may be used. The transformer 310 serves to boost the voltage supplied through the switch 270 according to the turns ratio of the primary coil to secondary coil. The high voltage is transformed by adjusting the voltage supplied to the primary side of the transformer 310 according to the pulse width generated by the pulse generating unit 260, and the maximum voltage applicable is, for example, DC 320 V. The transformer 310 is boosted up to AC 150 kV according to the turns ratio, the AC voltage is converted to DC voltage through a full-wave rectification circuit, and then transmitted to the X-ray tube 2000 through the high voltage switch 320. Meanwhile, the transformer 310 may further include a filament transformer for driving a filament in the X-ray tube 2000. The filament transformer applies a voltage determined by the pulse signal generated from the pulse control unit 200 to the primary coil of the filament transformer, and about 10 to 30 V is output depending on the turns ratio. The output voltage is supplied to the cathode of the X-ray tube 2000 and drives the filament in the X-ray tube 2000, which is a dipole vacuum tube, to emit hot electrons.

1.3.2. High Voltage Switch

The high voltage switch 320 is provided between the transformer 310 and the X-ray tube 2000. The high voltage switch 320 controls the application of the high voltage to the X-ray tube 2000 by switching the high voltage generated by the transformer 310.

1.3.3. Voltage Detecting Unit

The voltage detecting unit 330 detects a high voltage generated from the transformer 310 and applied to the X-ray tube 2000 through the high voltage switch 320. Here, the voltage detecting unit 330 may be composed of, for example, a division resistor, and a high voltage may be divided through the division resistor and a DC voltage corresponding to the high voltage may be output. In this way, the DC voltage output through the voltage detecting unit 330 is used as a feedback signal for the tube voltage control. That is, the feedback signal according to the high voltage detected by the voltage detecting unit 330 may be applied to the pulse generating unit 260 to be used for generation of the pulse signal. That is, the pulse generating unit 260 receives the tube voltage feedback signal from the voltage detecting unit 330 and compares the generated pulse signal with the actual tube voltage to always generate a uniform pulse signal.

1.3.4. Current Detecting Unit

The current detecting unit 340 detects a filament current of the X-ray tube 2000. Here, the current detecting unit 340 may be composed of a predetermined current sensor. In addition, in the current detecting unit 340, it is converted into a small signal DC voltage corresponding to the filament current and is used as a feedback signal of the tube current control.

2. X-Ray Tube

The X-ray tube 2000 is configured with a cathode that emits electrons and an anode that generates X-rays by colliding with the emitted electrons. The X-ray tube 2000 may use a rotating anode to reduce damage to the anode target and dissipate heat so as to effectively generate X-rays, and may be composed of a bearing, a shaft, a tungsten target, etc. When power is supplied to a stator coil, the anode rotor rotates at a high speed of about 3,200 rpm by the rotating magnetic field. When power is supplied and the cathode filament is heated, the cathode filament emits hot electrons, and when a high voltage of 20 kV or more is supplied between the anode and cathode of the X-ray tube, the emitted electrons collide with the anode target at high speed to generate X-rays.

As described above, in the voltage generating apparatus 1000 according to an embodiment of the present inventive concept, the console 100 can detect the X-ray irradiation signal to generate a predetermined detection signal, and the pulse control unit 200 can detect the detection signal from the console 100 to control the generation of the pulse signal. That is, in the present inventive concept, the console 100 may include the first signal detecting unit 140 that detects an X-ray irradiation signal to generate the first detection signal and the pulse control unit 200 may include the second signal detecting unit 230 that detects the control signal and the first detection signal from the console 100 to generate the second detection signal. In this case, when both the first control signal and the first detection signal from the console 100 are applied at high levels, the second signal detecting unit 230 of the pulse control unit 200 may generate the second detection signal and apply the second detection signal to the high voltage generating unit 300. Since the pulse control unit 200 generates the second detection signal according to the first detection signal and the first control signal and generates the pulse signal for generating a high voltage accordingly, the malfunction due to damage to the components constituting the console 100 and/or the pulse control unit 200 can be prevented. That is, conventionally, since the pulse control unit 200 operates only with the control signal, the malfunction has occurred due to damage to the components constituting the console 100 and/or the pulse control unit 200. However, in the present inventive concept, the pulse signal is generated according to the control signal and the detection signal generated according to the X-ray irradiation signal, erroneous generation of the pulse signal can be prevented, and accordingly, the malfunction of the X-ray generating apparatus can be prevented.

As described above, in one embodiment of the present inventive concept, the first signal detecting unit 140 is provided in the console 100 and the second signal detecting unit 230 is provided in the pulse control unit 200 to control the generation of pulses according to the X-ray irradiation signal and the detection signal. Meanwhile, various modifications may be made to the present inventive concept for controlling pulse generation by generating a detection signal according to an X-ray irradiation signal. An X-ray irradiation apparatus according to another embodiment of the present inventive concept is illustrated in FIG. 4. As illustrated in FIG. 4, in the other embodiment of the present inventive concept, one signal detecting unit 230A is provided in the pulse control unit 200. That is, in contrast to the embodiment of the present inventive concept illustrated in FIG. 2, in the other embodiment of the present inventive concept illustrated in FIG. 4, the first signal detecting unit 140 is not provided in the console 100, but the signal detecting unit 230A is provided in the pulse control unit 200. In this case, the signal detecting unit 230A receives and detects the output signal of the second control unit 240.

The second control unit 240 receives the first control signal from the console 100 to generate the third control signal and generates the fourth control signal generated by setting the tune voltage, the tube current, the irradiation time, etc. In addition, the second control unit 240 detects any one of the first and second control signals according to the X-ray irradiation signal to generate a detection signal, and transmits the detection signal to the signal detecting unit 230A. That is, the second control unit 240 may generate the detection signal as well as the third and fourth control signals. In this case, the second control unit 240 may be separately provided with a signal detecting unit for generating a detection signal as in the embodiment of the present inventive concept described with reference to FIG. 2. Since the second control unit 240 is implemented as a microprocessor, a part for generating the control signal and a part for generating the detection signal may be separately provided. However, in the other embodiment of the present inventive concept, it has been described that the second control unit 240 generates the third and fourth control signals and the detection signals. Therefore, in the other embodiment of the present inventive concept, the second control unit 240 in the pulse control unit 200 generates the detection signal, and the signal detecting unit 230A combines the third control signal and the detection signal and outputs the combination of the third control signal and the detection signal to the pulse generating unit 260, so that the pulse generation of the pulse generating unit 260 may be controlled.

Although the voltage generating apparatus and X-ray generating apparatus having the same have been described with reference to the specific embodiments, it should be noted that they are for explanatory purposes and are not limited thereto. Therefore, it will be readily understood by those skilled in the art that various modifications and changes can be made thereto without departing from the spirit and scope of the present inventive concept defined by the appended claims.

What is claimed is:

1. A voltage generating apparatus comprising:
a console configured to receive an X-ray irradiation signal to generate a control signal and detect the X-ray irradiation signal to generate a first detection signal;
a pulse control unit configured to receive the control signal and the first detection signal from the console to generate a second detection signal, and generate a pulse signal according to the control signal and the second detection signal; and
a high voltage generating unit configured to generate a high voltage according to the pulse signal from the pulse control unit,
wherein the console comprises:
a first control unit configured to receive the X-ray irradiation signal to generate the control signal; and
a first signal detecting unit configured to detect the X-ray irradiation signal to generate the first detection signal,
wherein the first control unit is configured to generate first and second control signals, respectively, and the first signal detecting unit is configured to generate the first detection signal according to a level of the X-ray irradiation signal.

2. The apparatus of claim 1, wherein
the pulse control unit comprises:
a second signal detecting unit configured to receive the first control signal and the first detection signal from the console and combine the first control signal and the first detection signal to generate the second detection signal;
a second control unit configured to receive the second control signal from the console and receive the second detection signal from the second signal detecting unit to generate third and fourth control signals;
a converter configured to convert the third control signal from the second control unit; and
a pulse generating unit configured to receive an output signal from the converter and the fourth control signal from the second control unit to generate the pulse signal.

3. The apparatus of claim 2, wherein
the pulse control unit further comprises a first input unit configured to receive the second control signal, a second input unit configured to receive the first control signal, and a switch configured to apply the pulse signal to the high voltage generating unit.

4. The apparatus of claim 3, wherein
the second signal detecting unit is configured to generate the second detection signal of a predetermined level according to the first control signal and the first detection signal each having a predetermined level or higher.

5. The apparatus of claim 3, wherein
the second signal detecting unit is configured to generate the second detection signal of a predetermined level when the X-ray irradiation signal is equal to or greater than a predetermined level and the first detection signal is greater than or equal to a predetermined level.

6. The apparatus of claim 4, wherein
the second signal detecting unit comprises a high-pass filter configured to receive the first detection signal, and at least one AND gate configured to combine an output of the high-pass filter and an output of the second input unit, and generate the second detection signal as an output of the AND gate.

7. The apparatus of claim 6, wherein
the second control unit is configured to receive the second control signal from the console and the second detection signal from the second signal detecting unit to generate the third and fourth control signals and output the third and fourth control signals to the pulse generating unit, respectively.

8. The apparatus of claim 7, wherein
the pulse generating unit is configured to receive the third control signal from the second control unit, the output signal from the converter, and a feedback signal from the high voltage generating unit to generate the pulse signal.

9. The apparatus of claim 8, wherein
the high voltage generating unit comprises:
a transformer configured to generate the high voltage to be applied to an X-ray tube according to the pulse signal from the pulse control unit;
a high voltage switch configured to control an application of the high voltage generated from the transformer to the X-ray tube;
a voltage detecting unit configured to detect the high voltage applied to the X-ray tube and feed the high voltage back to the pulse generating unit; and
a current detecting unit configured to detect a current of the X-ray tube.

10. An X-ray generating apparatus comprising:
a voltage generating apparatus configured to generate a predetermined voltage according to an X-ray irradiation signal; and
an X-ray tube configured to generate X-rays according to a voltage from the voltage generating apparatus, wherein
the voltage generating apparatus includes a signal detecting unit configured to detect the X-ray irradiation signal to generate a detection signal, and configured to generate the predetermined voltage according to the X-ray irradiation signal and the detection signal,
wherein the voltage generating apparatus comprises:
a console configured to receive the X-ray irradiation signal to generate a control signal and detect the X-ray irradiation signal to generate a first detection signal;
a pulse control unit configured to receive the control signal and the first detection signal from the console to generate a second detection signal and generate a pulse signal according to the control signal and the second detection signal; and
a high voltage generating unit configured to generate a high voltage according to the pulse signal from the pulse control unit,
wherein the console comprises:
a first control unit configured to receive the X-ray irradiation signal to generate first and second control signals, respectively; and
a first signal detecting unit configured to detect the X-ray irradiation signal to generate a first detection signal; and
wherein the voltage generating apparatus comprises:
a second signal detecting unit configured to receive the first control signal and the first detection signal and combine the first control signal and the first detection signal to generate a second detection signal;
a second control unit configured to receive the second control signal and receive the second detection signal from the second signal detecting unit to generate third and fourth control signals;
a converter configured to convert the third control signal from the second control unit; and
a pulse generating unit configured to receive an output signal from the converter and the fourth control signal from the second control unit to generate the pulse signal.

11. The apparatus of claim 10, wherein
the second signal detecting unit is configured to output the first detection signal, which is input through a high-pass filter, and the first control signal through at least one AND gate to generate the second detection signal.

12. An X-ray generating apparatus comprising:
a voltage generating apparatus configured to generate a predetermined voltage according to an X-ray irradiation signal; and
an X-ray tube configured to generate X-rays according to a voltage from the voltage generating apparatus,
wherein the voltage generating apparatus includes a signal detecting unit configured to detect the X-ray irradiation signal to generate a detection signal, and configured to generate the predetermined voltage according to the X-ray irradiation signal and the detection signal,
wherein the voltage generating apparatus comprises:
a console configured to receive the X-ray irradiation signal to generate a control signal;
a pulse control unit configured to receive the control signal from the console to generate the detection signal and configured to generate a pulse signal according to the control signal and the detection signal; and
a high voltage generating unit configured to generate a high voltage according to the pulse signal from the pulse control unit,
wherein the console comprises a first control unit configured to receive the X-ray irradiation signal to generate first and second control signals, respectively, and
wherein the voltage generating apparatus comprises:
a second control unit configured to receive the first and second control signals from the console to generate third and fourth control signals, respectively, and configured to detect at least one of the first and second control signals to generate a first detection signal;
a second signal detecting unit configured to receive the fourth control signal and the first detection signal and combines the fourth control signal and the first detection signal to generate a second detection signal;
a converter configured to convert the third control signal from the second control unit; and
a pulse generating unit configured to receive an output signal from the converter and the second detection signal from the second signal detecting unit to generate the pulse signal.

* * * * *